US012708254B2

(12) United States Patent
McDowall

(10) Patent No.: US 12,708,254 B2
(45) Date of Patent: Aug. 18, 2026

(54) IMAGING SYSTEMS WITH MULTIPLE FOLD OPTICAL PATH

(71) Applicant: INTUITIVE SURGICAL OPERATIONS, INC., Sunnyvale, CA (US)

(72) Inventor: Ian E. McDowall, Woodside, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 301 days.

(21) Appl. No.: 18/580,694

(22) PCT Filed: Jul. 13, 2022

(86) PCT No.: PCT/US2022/036974
§ 371 (c)(1),
(2) Date: Jan. 19, 2024

(87) PCT Pub. No.: WO2023/003734
PCT Pub. Date: Jan. 26, 2023

(65) Prior Publication Data

US 2024/0366074 A1 Nov. 7, 2024

Related U.S. Application Data

(60) Provisional application No. 63/225,197, filed on Jul. 23, 2021.

(51) Int. Cl.
*A61B 5/00* (2006.01)
*A61B 1/00* (2006.01)
(Continued)

(52) U.S. Cl.
CPC ...... *A61B 1/00193* (2013.01); *A61B 1/00096* (2013.01); *A61B 1/051* (2013.01); *A61B 1/128* (2013.01)

(58) Field of Classification Search
CPC . A61B 1/00193; A61B 1/00096; A61B 1/051; A61B 1/128
See application file for complete search history.

(56) References Cited

U.S. PATENT DOCUMENTS

2013/0041221 A1* 2/2013 McDowall ............. H04N 23/56 348/E9.037
2014/0378769 A1* 12/2014 Rehe .................. G02B 23/2446 600/176
(Continued)

OTHER PUBLICATIONS

International Search Report and Written Opinion for Application No. PCT/US2022/036974, mailed Oct. 28, 2022, 13 pages.
(Continued)

*Primary Examiner* — Joel F Brutus
(74) *Attorney, Agent, or Firm* — Haynes & Boone, LLP.

(57) ABSTRACT

An endoscopic system may comprise a first objective lens assembly extending along a first side of a central longitudinal axis through the endoscopic system and a second objective lens assembly extending along a second side of the central longitudinal axis. The endoscopic system may also comprise a prism assembly at a proximal end of the first and second objective lens assemblies, a first image capture sensor coupled to the prism assembly on the first side of the central longitudinal axis, and a second image capture sensor coupled to the prism assembly on the second side of the central longitudinal axis. The prism assembly may direct first light from the first objective lens assembly to the second image capture sensor.

20 Claims, 8 Drawing Sheets

(51) Int. Cl.
*A61B 1/05* (2006.01)
*A61B 1/12* (2006.01)

(56) References Cited

U.S. PATENT DOCUMENTS

| | | | | |
|---|---|---|---|---|
| 2016/0004065 | A1* | 1/2016 | Zobel | G02B 23/243 359/462 |
| 2016/0178886 | A1 | 6/2016 | Shechterman et al. | |
| 2016/0306180 | A1 | 10/2016 | Rosa | |
| 2018/0103246 | A1* | 4/2018 | Yamamoto | A61B 1/04 |
| 2021/0121045 | A1* | 4/2021 | Levy | A61B 1/00068 |

OTHER PUBLICATIONS

Vertut, J., and Coiffet, P., “Robot Technology: Teleoperation and Robotics Evolution and Development,” English translation, Prentice-Hall, Inc., Inglewood Cliffs, NJ, USA 1986, vol. 3A, 332 pages.
International Preliminary Report on Patentability for Application No. PCT/US2022/036974, mailed Feb. 1, 2024, 07 pages.

* cited by examiner

IMAGING SYSTEMS WITH MULTIPLE FOLD OPTICAL PATH

CROSS-REFERENCED APPLICATIONS

This application is the U.S. national phase of International Application No. PCT/US2022/036974, filed Jul. 13, 2022, which designated the U.S. and claims priority to and the benefit of U.S. Provisional Application No. 63/225,197, filed Jul. 23, 2021, entitled "Imaging Systems with Multiple Fold Optical Path," all of which are incorporated by reference herein in their entirety.

TECHNICAL FIELD

Examples described herein are related to stereoscopic imaging systems with an optical assembly that directs light along optical paths through multiple folds toward image sensors.

BACKGROUND

Minimally invasive medical techniques may generally be intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions an operator may insert minimally invasive medical instruments to reach a target tissue location. Minimally invasive medical tools include instruments such as therapeutic instruments, diagnostic instruments, imaging instruments, and surgical instruments. In some examples, a minimally invasive medical tool may be a stereo-imaging instrument, such as a stereoscopic endoscope, for generating three-dimensional images of anatomic areas within a patient anatomy. Stereo-imaging instruments may include a pair of objective lens assemblies for directing light to an image sensing system to generate a stereo pair of images.

SUMMARY

The following presents a simplified summary of various examples described herein and is not intended to identify key or critical elements or to delineate the scope of the claims.

In some examples, an endoscopic system may comprise a first objective lens assembly extending along a first side of a central longitudinal axis through the endoscopic system and a second objective lens assembly extending along a second side of the central longitudinal axis. The endoscopic system may also comprise a prism assembly at a proximal end of the first and second objective lens assemblies, a first image capture sensor coupled to the prism assembly on the first side of the central longitudinal axis, and a second image capture sensor coupled to the prism assembly on the second side of the central longitudinal axis. The prism assembly may direct first light from the first objective lens assembly to the second image capture sensor.

In another example, a medical instrument system may comprise a control system and an endoscopic device through which extends a longitudinal axis. The control system may comprise a processor and a memory comprising machine readable instructions that, when executed by the processor, cause the control system to direct first light through a first objective lens assembly of the endoscopic device, to direct the first light through a first surface of a first lateral prism of the endoscopic device, to direct the first light toward a second surface of the first lateral prism, to reflect the first light toward a third surface of the first lateral prism, to reflect the first light from the third surface toward the second surface of the first lateral prism, to transmit the first light through the second surface of the first lateral prism and into a central prism of the endoscopic device and to receive the first light a first image capture sensor adjacent to the central prism. The first image capture sensor may be on an opposite side of the longitudinal axis from the first objective lens assembly.

It is to be understood that both the foregoing general description and the following detailed description are illustrative and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
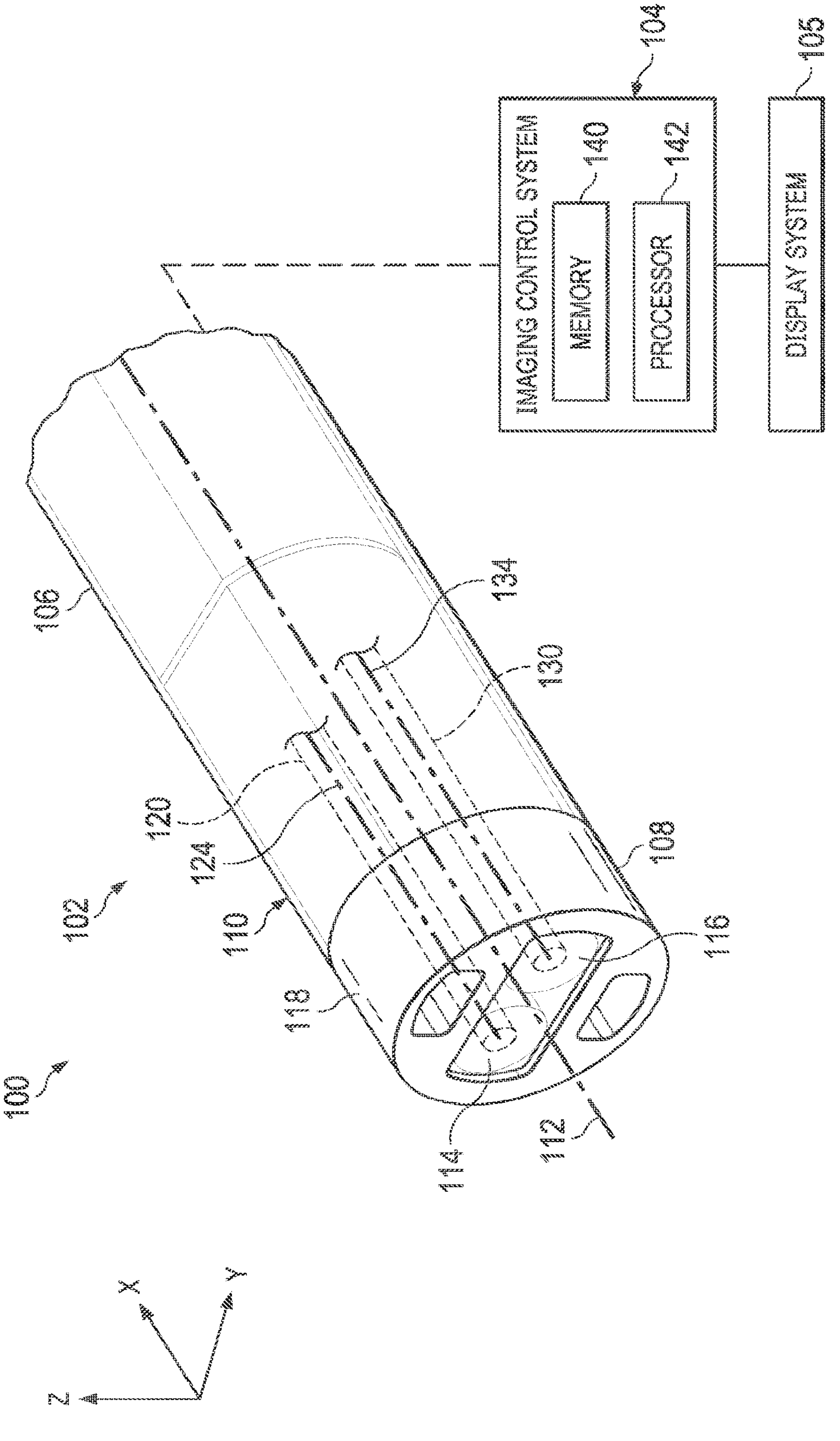
FIG. 1 illustrates a distal end of a stereoscopic imaging system according to some examples.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The technology described herein provides stereoscopic imaging systems that include an optical assembly that directs light along an optical path through multiple folds toward an image sensor. The folded optical path may allow for the arrangement of imaging sensors with large image capture surfaces to capture larger and/or higher resolution images. Stereoscopic imaging systems described herein may also utilize entrance pupil distances that provide correct stereo vision geometry.

FIG. 1 illustrates a stereoscopic imaging system 100 that may be a stereoscopic endoscope system in some examples. The stereoscopic imaging system 100 may include an imaging instrument 102 coupled to an imaging control system 104. The imaging control system 104 may provide imaging signals for display on a display system 105. The imaging instrument 102 may be in an environment having a Cartesian coordinate system X, Y, Z. The imaging instrument 102 may include an elongate body 106 and an imaging device 108 that is coupled to a distal end 110 of the elongate body 106. A longitudinal axis 112 may extend through the imaging instrument 102. The elongate body 106 may be flexible or rigid, and the distal end 110 may be inserted into a patient anatomy to obtain stereoscopic images of anatomic tissue. In some examples, the patient anatomy may be a patient trachea, lung, colon, intestines, stomach, liver, kidneys and kidney calices, brain, heart, circulatory system including vasculature, and/or the like.

The imaging device 108 includes a right objective lens assembly 114 and a left objective lens assembly 116 inside of a housing 118. In the example of FIG. 1, the housing 118 may extend at least partially into a distal opening of the elongate body 106. In other examples, the housing 118 may extend over or abut to the distal end 110 of the elongate body 106. The right objective lens assembly 114 and the left objective lens assembly 116 may be arranged symmetrically about the longitudinal axis 112. Light 120 (e.g. first light) entering the right objective lens assembly 114 may extend along an optical axis 124 of the objective lens assembly 114. The light 120 may be centered about or symmetrical about the optical axis 124. Light 130 (e.g., second light) entering the left objective lens assembly 116 may extend along an optical axis 134 the objective lens assembly 116. The light 130 may be centered about or symmetrical about the optical axis 134.

In some examples, the imaging instrument 102 may also include auxiliary systems such as illumination systems, cleaning systems, irrigation systems and/or other systems (not shown) to assist the function of the imaging device 108. In some examples, the imaging instrument 102 may also house cables, linkages, or other steering controls (not shown) to effectuate motion (e.g., pitch and yaw motion) of the distal end 110 of the elongate body 106.

The imaging control system 104 may include at least one memory 140 and at least one computer processor 142 for effecting control of imaging instrument 102, including recording image data, sending signals to and receiving information and/or electrical signals from the imaging assembly, operating an auxiliary system, moving the imaging device 108, and/or other functions of the imaging instrument 102. In some embodiments, the imaging control system 104 may be coupled to or be a component of a control system of a robot-assisted medical system. The imaging control system 104 may also include programmed instructions (e.g., a non-transitory machine-readable medium storing the instructions) to implement some or all of the methods described in accordance with aspects disclosed herein.

Figure 2:
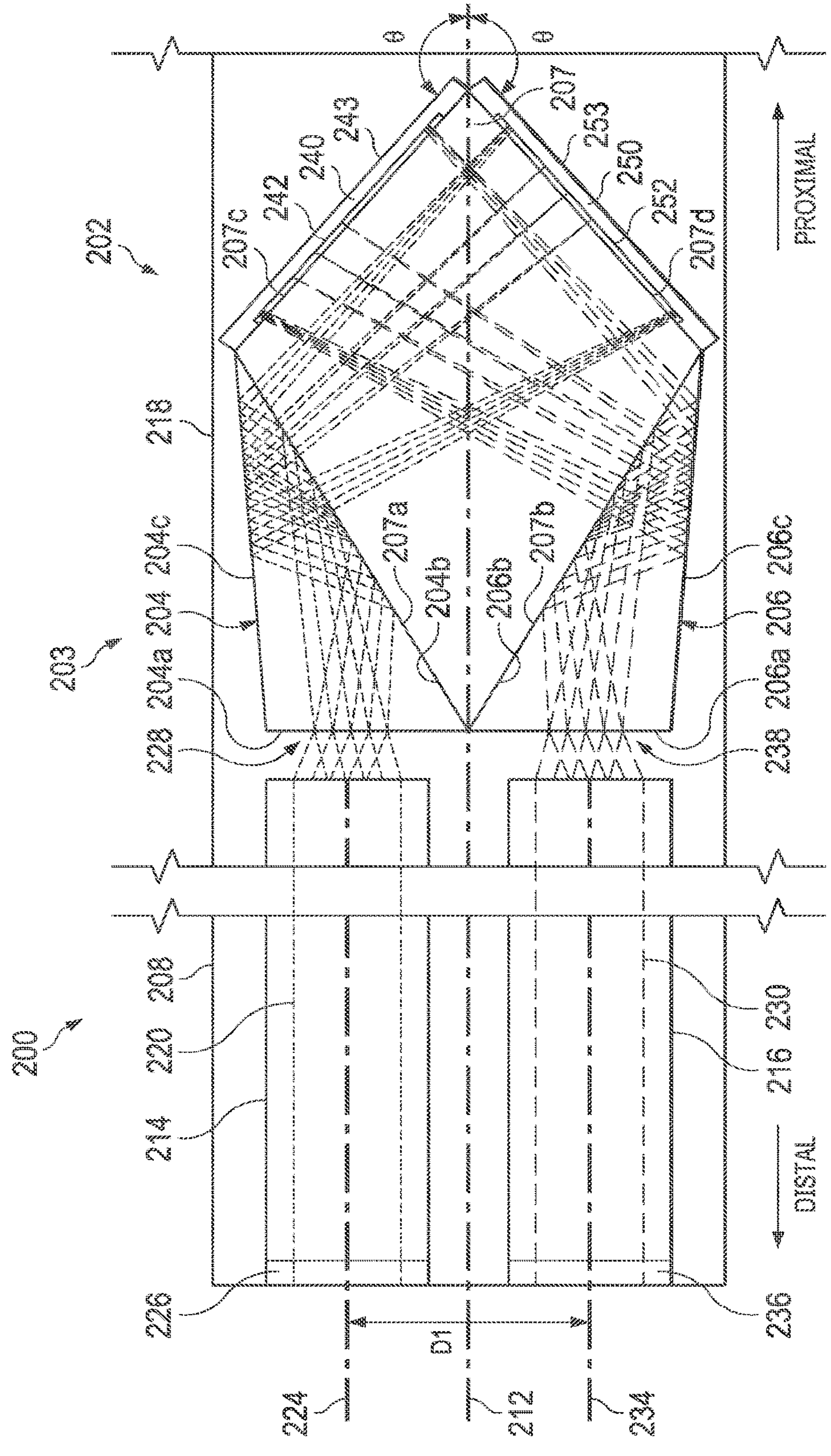
FIG. 2 is a schematic illustration of a stereoscopic imaging system including a pair of imaging assemblies, a prism assembly, and a pair of imaging sensors according to some examples.

FIG. 2 provides a schematic illustration of a stereoscopic imaging system 200 (e.g., imaging system 100) which may be a stereoscopic endoscope system. The stereoscopic imaging system 200 includes an imaging instrument 202. The imaging instrument 202 may include an imaging device 208. A longitudinal axis 212 may extend through the imaging instrument 202. The imaging device 208 may include a right objective lens assembly 214 (e.g., a first objective lens assembly) and a left objective lens assembly 216 (e.g. a second objective lens assembly) inside of a housing 218. The right objective lens assembly 214 and the left objective lens assembly 216 may be arranged symmetrically about the longitudinal axis 212. The imaging device 208 may also include a prism assembly 203, arranged proximally of the right objective lens assembly 214 and the left objective lens assembly 216, within the housing 218. The prism assembly 203 may include a right lateral prism 204, a left lateral prism 206, and a central prism 207. The imaging device 208 may also include a right image capture sensor 240 and a left image capture sensor 250 inside of the housing 218.

The objective lens assembly 214 may include a single lens or may include a plurality of lenses, mirrors, prisms, and/or other optical elements to direct light 220 (e.g., first light) along the optical axis 224 between an entrance pupil 226 at a distal end of the objective lens assembly 214 and an exit pupil 228 near a proximal end of the objective lens assembly 214. The objective lens assembly 216 may include a single lens or may include a plurality of lenses, mirrors, prisms, and/or other optical elements to direct light 230 (e.g., second light) along the optical axis 234 between an entrance pupil 236 at a distal end of the objective lens assembly 216 and an exit pupil 238 near a proximal end of the objective lens assembly 216. An interpupillary distance D1 extends between the centers of the entrance pupils 226 and 236. To maintain an undistorted stereo disparity in the recorded stereo image pair, the ratio of the interpupillary distance D1 to the distance to viewed object, may be approximately the same as the ratio of the distance between the viewer's eyes to the distance to the stereo display. For some systems comprising a stereo display at close range to the viewer, the interpupillary distance may be between approximately 1 mm and 6 mm and in some examples may be between approximately 3.5 mm and 4.6 mm. For some systems comprising a stereo display viewed from a greater distance, the interpupillary distance may be smaller. If the entrance pupils are closer together than preferred, the disparity between the images in the stereo pair may be less than preferred and the viewer's sense of depth perception may be reduced. If, however, the distance between the entrance pupils is greater than preferred, the disparity is also greater, resulting in an exaggerated sense of depth perception and images that may be difficult to fuse and uncomfortable to watch. Machine vision applications may have other interpupillary distance requirements that may be addressed by the imaging systems described herein.

In the example of FIG. 2, the right lateral prism 204 may include a first surface 204*a*, a second surface 204*b*, and a third surface 204*c*. The left lateral prism 206 may include a first surface 206*a*, a second surface 206*b*, and a third surface 206*c*. The central prism 207 may include a right entrance surface 207*a*, a left entrance surface 207*b*, a right exit surface 207*c*, and a left exit surface 207*d*. The right image capture sensor 240 may include a right image capture surface 242 adjacent to the right exit surface 207*c* and a right back surface 243 opposite the right image capture surface. The left image capture sensor 250 may include a left image capture sensor surface 252 adjacent to the left exit surface 207*d* and a left back surface 253 opposite the left image capture surface 252.

Light 220 entering the right objective lens assembly 214 may extend along an optical axis 224 of the objective lens assembly 214. The light 220 may be centered about or symmetrical about the optical axis 224. Light 230 entering the left objective lens assembly 216 may extend along an optical axis 234 of the objective lens assembly 216. The light 230 may be centered about or symmetrical about the optical axis 234. In this example, the optical axes 224, 234 may be generally parallel to the longitudinal axis 212, but in other examples may be non-parallel to the longitudinal axis 212.

The light 220 exiting the exit pupil 228 of the right objective lens assembly 214 may enter the right lateral prism 204 through the surface 204*a* and may be directed through the prism 204 toward the surface 204*b*. The light 220 may encounter the surface 204*b* at an angle such that the surface 204*b* may reflect all or substantially all of the light 220 back into the prism 204 and toward the surface 204*c*. This reflection at the surface 204*b* may occur because of total internal reflection at the surface 204*b* caused by an incident angle greater than a critical angle and by a lower index of refraction of a medium adjacent to the surface 204*b*. For example, total internal reflection may result when the central prism 207 or a fluid (e.g. air) located in a gap between surfaces 204*b* and 207*a* has an index of refraction appropriately less than the index of refraction of the right lateral prism 204. The surface 204*c* may reflect all or substantially all of the light 220 inside the prism 204 and toward the surface 204*b*. When the light 220 encounters the surface 204*b* the second time, the angle of incidence may be approximately perpendicular (or at least smaller than the critical angle) to the surface 204*b*, allowing the light 220 to pass through the surface 204*b*. The light 220 may exit through the surface 204*b* and enter the central prism 207 through the right entrance surface 207*a*. From the surface 207*a*, the light 220 may expand as it crosses the longitudinal axis 212 and is directed toward the left exit surface 207*d*. The expanded light 220 may pass through the left exit surface 207*d* and onto the left image capture surface 252 of the sensor 250.

The light 230 exiting the exit pupil 238 of the left objective lens assembly 216 may enter the left lateral prism 206 through the surface 206*a* and may be directed through the prism 206 toward the surface 206*b*. The light 230 may encounter the surface 206*b* at an angle such that the surface 206*b* may reflect all or substantially all of the light 230 back into the prism 206 and toward the surface 206*c*. This reflection at the surface 206*b* may occur because of total internal reflection at the surface 206*b* caused by an incident angle greater than a critical angle and by a lower index of refraction of a medium adjacent to the surface 206*b*. For example, total internal reflection may result when the central prism 207 or a fluid (e.g. air) located in a gap between surfaces 206*b* and 207*b* has an index of refraction appropriately less than the index of refraction of the left lateral prism 206. The surface 206*c* may reflect all or substantially all of the light 230 back inside the prism 206 and toward the surface 206*b*. When the light 230 encounters the surface 206*b* the second time, the angle of incidence may be approximately perpendicular (or at least smaller than the critical angle) to the surface 206*b*, allowing the light 230 to pass through the surface 206*b*. The light 230 may exit through the surface 206*b* and enter the central prism 207 through the left entrance surface 207*b*. From the surface 207*b*, the light 230 may expand as it crosses the longitudinal axis 212 and is directed toward the right exit surface 207*c*. The expanded light 220 may pass through the right exit surface 207*c* and onto the left image capture surface 242 of the sensor 240. In some examples, the initial incidence of the light on the 204*b*/206*b* surface may be reflected without total internal reflection, instead sliding the rays of light so they do not self-intersect.

The image capture sensors 240, 250 may be coupled to the central prism 207 (e.g. by an adhesive), may be positioned in abutment to the central prism 207 without coupling, or may be adjacent to but spaced slightly apart from the central prism 207. The image capture sensors 240, 250 may each be arranged such that an acute angle is formed between the image capture surfaces 242, 252 and the longitudinal axis 212. In greater detail, the image capture sensors 240, 250 may be arranged at an angle θ relative to the longitudinal axis 212, and the angle θ may be defined by the shape of the central prism 207. The angle θ may be, for example, greater than 135°, allowing for larger image capture surfaces 242, 252 and/or a smaller housing 218 diameter as compared to examples in which the angle θ may be 90° or 135°. To accommodate even larger image capture surfaces 242, 252 within the confines of the housing 218 or to accommodate a smaller housing 218 diameter, the angle θ may be greater than 135°. In this example, left and right eyes may not be aligned exactly on the centers of the image capture surfaces 242, 252. In some examples, an offset of approximately 1.1 mm from the center for each sensor may be permissible, thus allowing for a gain in sensor size of approximately 2.2 mm or approximately 1400 pixels at 1.55 μm. This offset may allow for a more natural interpupillary distance D1 (e.g., 1-6 mm). In some examples the angle θ may be different for imaging sensors 240 and 250.

Figure 3:
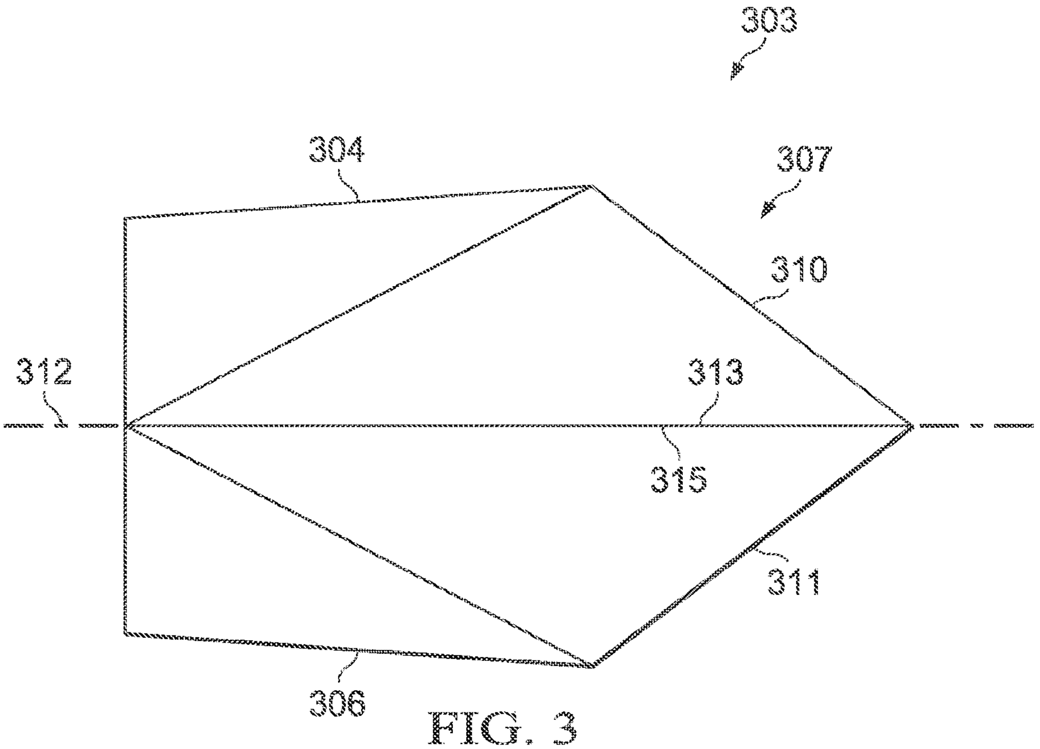
FIG. 3 illustrates a prism assembly according to some examples.

FIG. 3 illustrates an alternative example of a prism assembly 303 that may be used in place of prism assembly 203. The prism assembly 303 may be a four-part structure including a right lateral prism 304, a left lateral prism 306, and a two-part central prism 307 including a portion 310 and a portion 311. The right lateral prism 304 may be substantially similar to right lateral prism 204. The left lateral prism 306 may be substantially similar to left lateral prism 206. The portions 310, 311 of the central prism 307 may extend along opposite sides of a longitudinal axis 312. The portions may be bonded (e.g. by an adhesive), may be positioned in abutment without bonding, or may be adjacent to but spaced slightly apart from each other. A surface 313 of the portion 310 or a surface 315 of the portion 311 may be coated with a wavelength dependent coating. A two-part central prism 307 may be used to redirect all or a portion of the light passing through the central prism. For example, and as described in greater detail at FIG. 7, a wavelength dependent coating used between the surfaces 313, 315 may filter the light, allowing some wavelengths to pass while reflecting other wavelengths.

Figure 4:
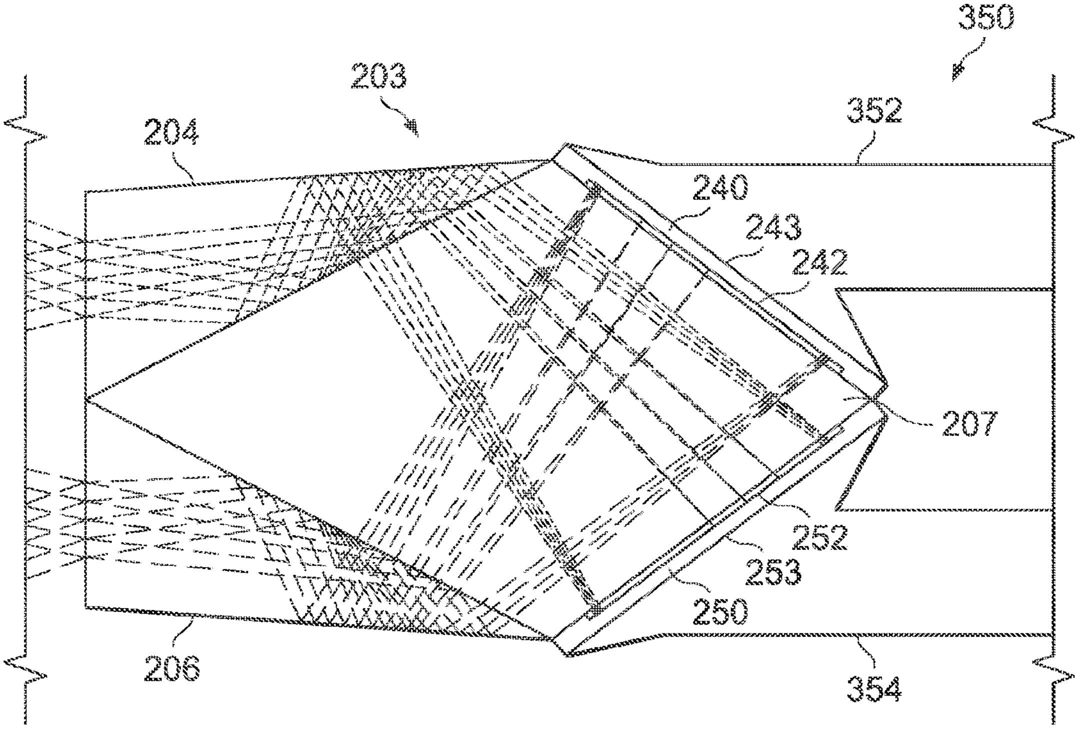
FIG. 4 illustrates a prism assembly and a thermal conduit system according to some examples.

FIG. 4 illustrates the prism assembly 203 with a thermal conduit system 350. In some examples, the left and right image capture sensors may each include a photodiode array in a stacked configuration with an analog to digital converter and other support electronic components. Heat generated by the image capture sensors may be conducted to the back surfaces 243, 253 to be drawn away from the sensors. Because the image capture sensor configuration allows for relatively large image capture sensors, the back surfaces may also have a relatively large surface area for heat dissipation. As compared to alternative designs that mount image sensors to a common substrate (e.g., a printed circuit board), the configuration of the image capture sensors in this example may leave the back surfaces 243, 253 relatively accessible for coupling to heat dissipation components of the thermal conduit system 350. A heat dissipation component 352 may be coupled to the back surface 243 of the right image capture sensor 240, and a heat dissipation component 354 may be coupled to the back surface 253 of the left image capture sensor 250. The heat dissipation components 352, 354 may be directly mounted to a substrate chip on which the image capture sensor is formed or may be coupled to the ball grid array of the image capture sensor. In some examples the heat dissipation component 354 may be a thermal conductor such as copper or aluminum or a heat pipe that couples to a proximal heat sink, which may be an endoscope handle. In some examples the heat dissipation components 352, 354 may be part of a fluid circulation system including fluid pumps and fluid conduits for circulating cooling fluid to the image capture sensors and transfer heat away from the sensors. In other examples, various other types of heat dissipation components may be used to cool the image capture sensors.

Figure 5A:
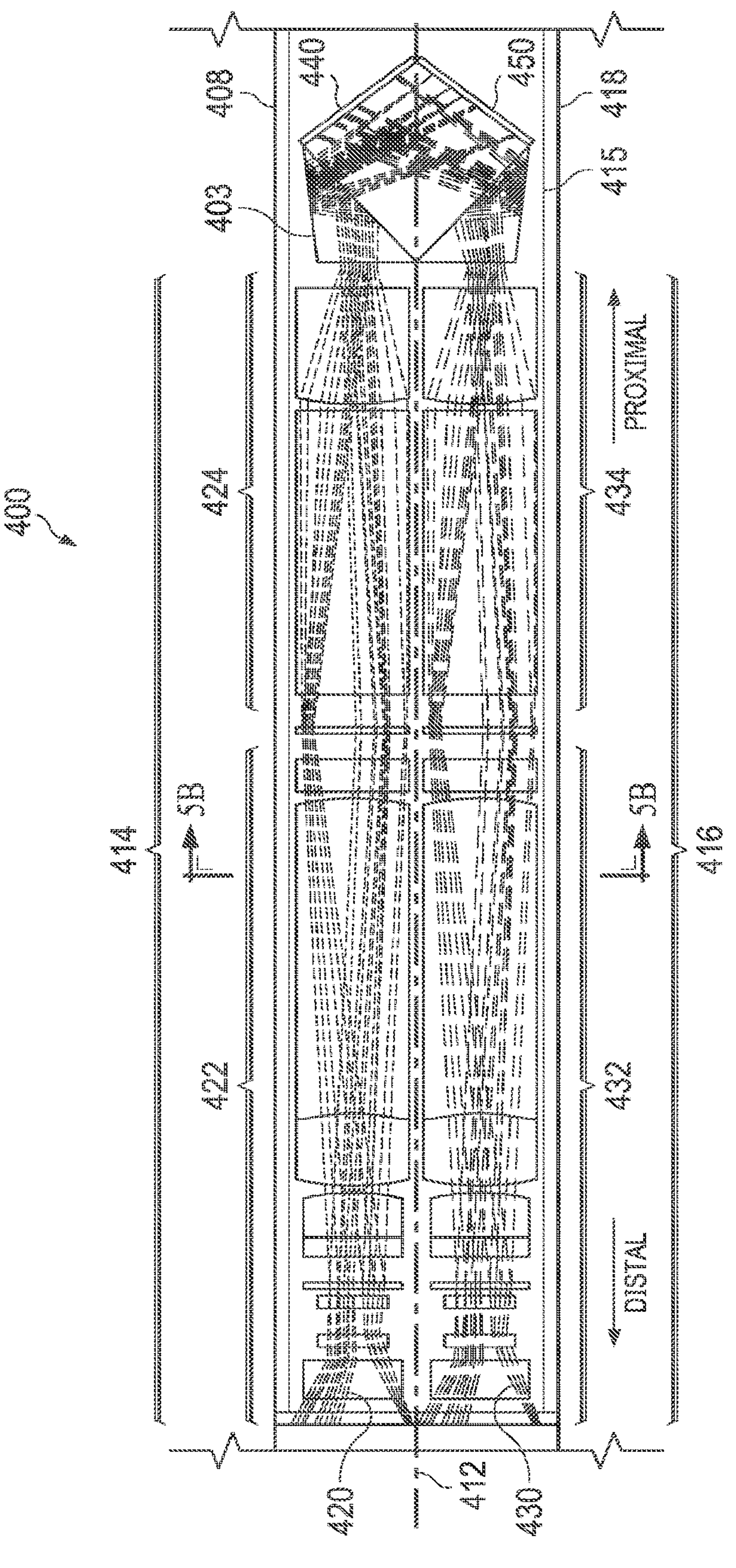
FIG. 5A is a schematic illustration of a stereoscopic imaging instrument including a pair of imaging assemblies, a prism assembly, and a pair of imaging sensors according to some examples.
Figure 5B:
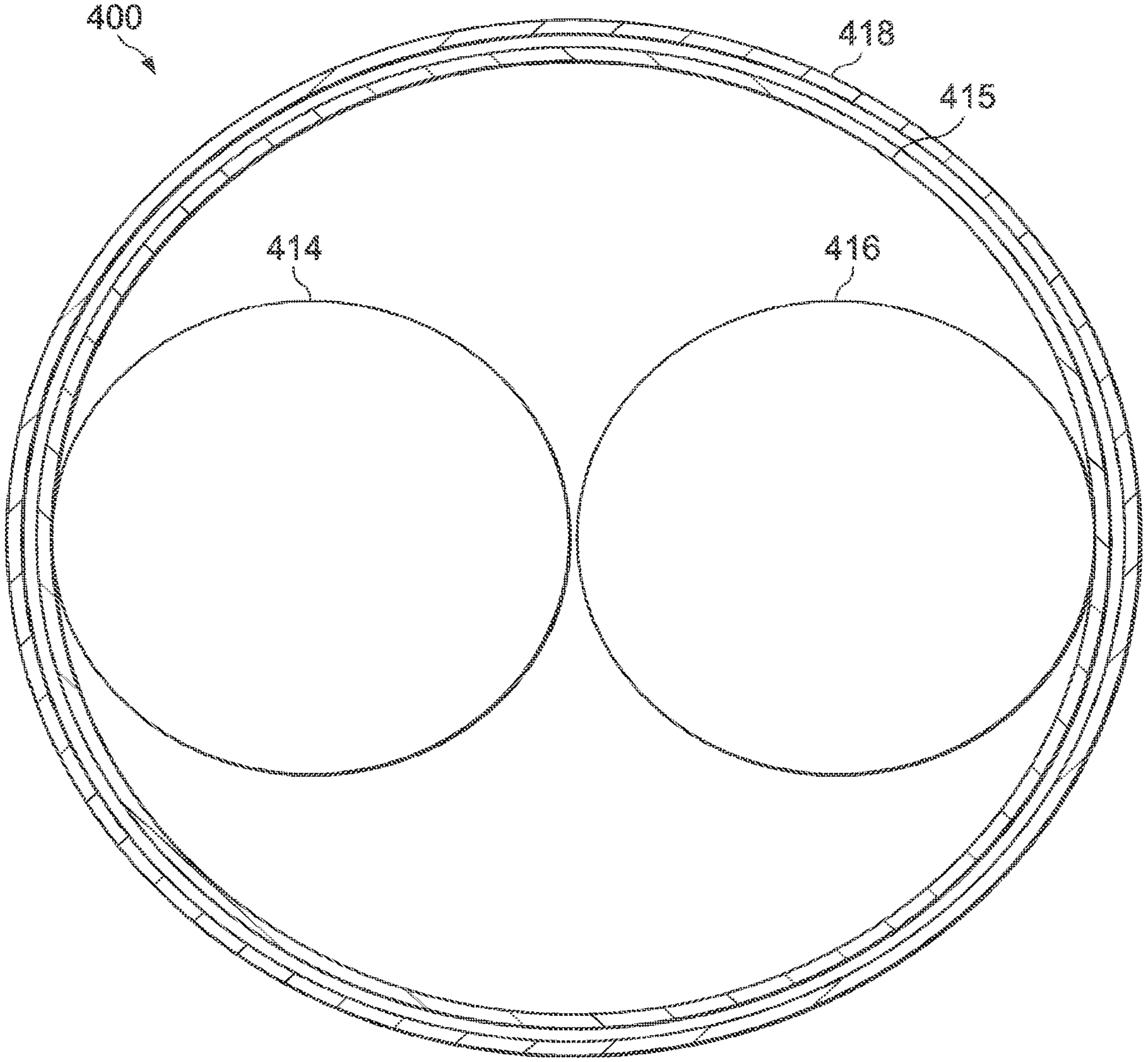
FIG. 5B is a cross-sectional view of the stereoscopic imaging instrument of FIG. 5A according to some examples.

FIG. 5A provides a schematic illustration of a stereoscopic imaging system 400 (e.g., imaging system 100) which may be a stereoscopic endoscope system. FIG. 5B is a cross-sectional view of the stereoscopic imaging instrument of FIG. 5A. The stereoscopic imaging system 400 may include an imaging device 408 which may be similar to the imaging device 208 except as described. A longitudinal axis 412 may extend through the imaging device 408. The imaging device 408 may include a right objective lens assembly 414 and a left objective lens assembly 416 coupled to a scaffolding 415 inside of a housing 418. The imaging device 408 may also include a prism assembly 403, arranged proximally of the right objective lens assembly 414 and the left objective lens assembly 416, within the housing 418. The prism assembly 403 may also be coupled to the scaffolding 415. The imaging device 408 may also include a right image capture sensor 440 and a left image capture sensor 450 coupled to the prism assembly 403 or directly to the scaffolding 415. The scaffolding 415 may be an external cage to which the imaging system components are coupled and may support the components from a surrounding structure rather than from one or more centralized internal beams. An external scaffold structure may allow the objective lens assemblies to be larger in diameter and positioned closer together than would be possible with a centralized beam support or spine. Thus, the interpupillary distance may also be minimized with an external scaffolding as compared to a centralized spine. The imaging system components may be coupled to the scaffolding 415 externally of the housing 418 and may be inserted as a unit into an elongate body (e.g., elongate body 106) of the imaging system. 400. In alternative examples, any of the objective lens assemblies, prism assembly, and/or image capture sensors may be coupled to or supported by the housing 418 or by a centralized beam that extends through the housing 418.

In this example, the right objective lens assembly 414 may include a distal optical train 422 and proximal optical train 424. Each of the optical trains may include a plurality of lenses, mirrors, prisms, and/or other optical elements to direct light 420. The left objective lens assembly 416 may include a distal optical train 432 and proximal optical train 434. Each of the optical trains may include a plurality of lenses, mirrors, prisms, and/or other optical elements to direct light 430. In some examples, the optical trains 422, 424, 432, 434 may be fixedly coupled to the scaffolding 415 and may be fixed relative to the housing 418. In some examples, the distal optical trains 422, 432 may be fixed relative to the scaffolding 415 and housing 418, and the proximal optical trains 424, 434 may be movable longitudinally relative to the housing 418. Movement of the proximal optical trains 424, 434 may allow the imaging system 400 to be focused using the imaging control system 104. Active focusing may permit sharp focusing, including focusing suitable for 4K (i.e., 4,000 pixel) resolution or greater. The right and left objective lens assemblies or any of the optical trains may be designed with lenses to balance aberrations, achieve desired distortions, and/or achieve desired depth of field. In some examples, the movement of the optical trains may be independently adjusted or may be adjusted together as a pair. In some examples, the proximal optical trains may be fixed relative to the housing while the distal optical trains are moveable longitudinally to focus the imaging system. In some examples, both the proximal and distal optical trains may be movable to focus the imaging system.

Figure 6:
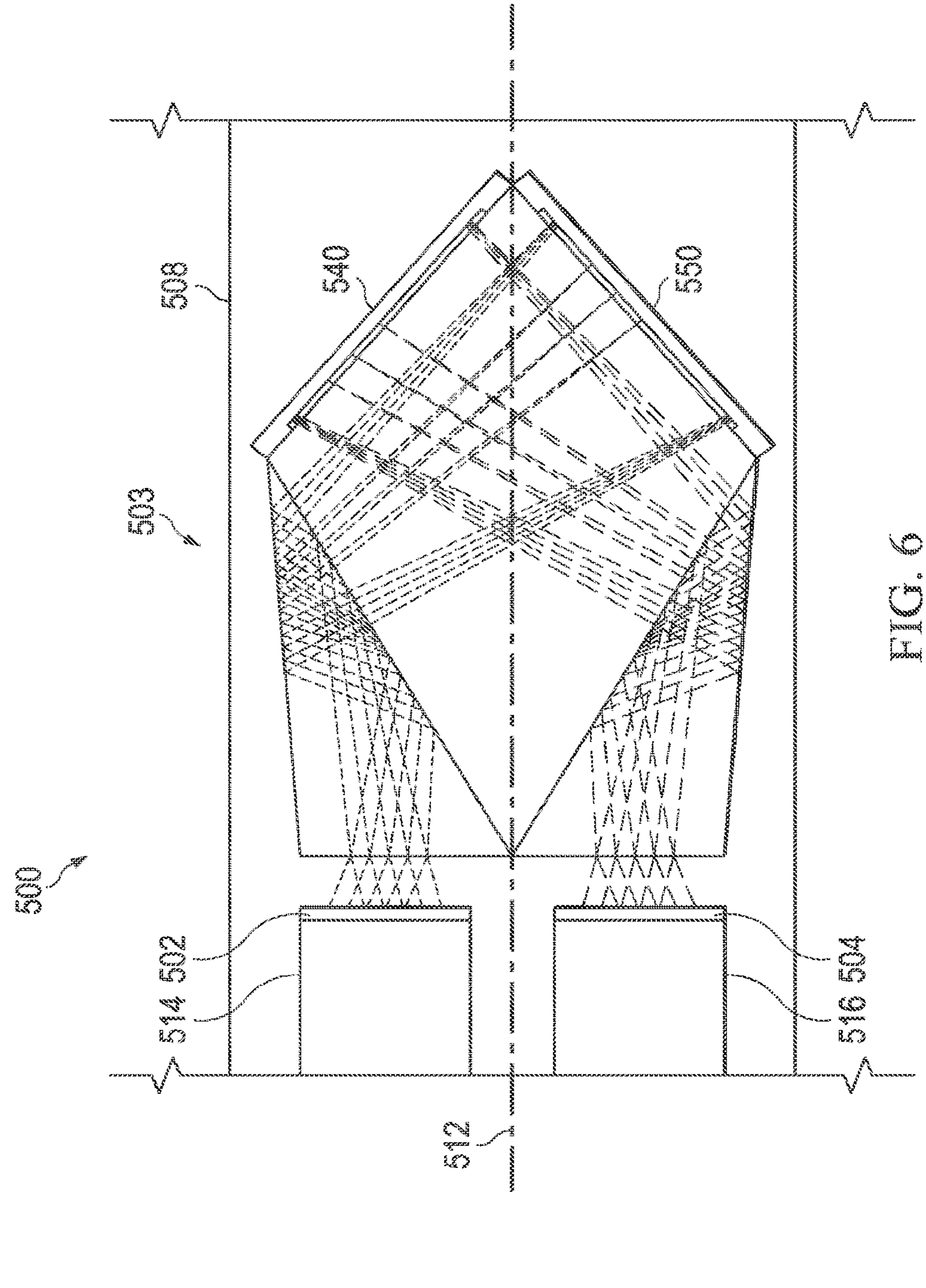
FIG. 6 is a schematic illustration of an imaging instrument including one or more filters according to some examples.

FIG. 6 provides a schematic illustration of a stereoscopic imaging system 500 (e.g., imaging system 100) which may be a stereoscopic endoscope system. The stereoscopic imaging system 500 may include an imaging device 508 which may be similar to the imaging device 208 except as described. A longitudinal axis 512 may extend through the imaging device 508. The imaging device 508 may include a right objective lens assembly 514, a left objective lens assembly 516, a prism assembly 503, a right image capture sensor 540 and a left image capture sensor 550. In this example, the right objective lens assembly 514 may include a right optical control device 502 and a left optical control device 504. One or both of the optical control devices 502, 504 may be a static or dynamically controllable filter that allows passage of selected wavelengths of light to the prism assembly 503. In the example of FIG. 6, the filter may be positioned at a proximal end of the objective lens assembly, but in other examples, the filter may be placed between or within optical trains of the objective lens assembly.

In one example, if the imaging system 500 uses illumination light in the visible and near infrared spectrums to image tissue that contains a fluorescent dye and if a laser excitation source is used to excite fluorescent dye in the tissue, the optical control devices 502, 504 may be filters selected to block excitation wavelengths in a range around the laser excitation source wavelength. Thus, light in the visible spectrum and light in the near infrared spectrum may pass through the filters 502, 504 to the prism assembly 503 and to the right and left image capture sensors 540, 550. The light received at the sensors 540, 550 may be separated by a control system (e.g. the control system 104) into different images based on the detected wavelength of light. For example, if the tissue is illuminated with visible blue light and laser excitation light, the sensors may detect near infrared light (e.g., as a result of fluorescence from fluorescent dye in the tissue) and the color blue corresponding to the visible blue light. The pair of image capture sensors may thus generate both grayscale (or black and white) stereoscopic images corresponding to the received blue light and fluorescent stereoscopic image corresponding to the received near infrared light. In alternative examples, the filters may be selected to filter different wavelengths and may have any of a variety of optical densities, including, for example an optical density of 4 or 6. In alternative examples, a filter may be present or operable to filter only one of the objective lens assemblies, allowing full transmission of light through the other objective lens assembly. In some examples, the filters may be adjustable and controlled by a control system such as imaging control system 104.

Figure 7:
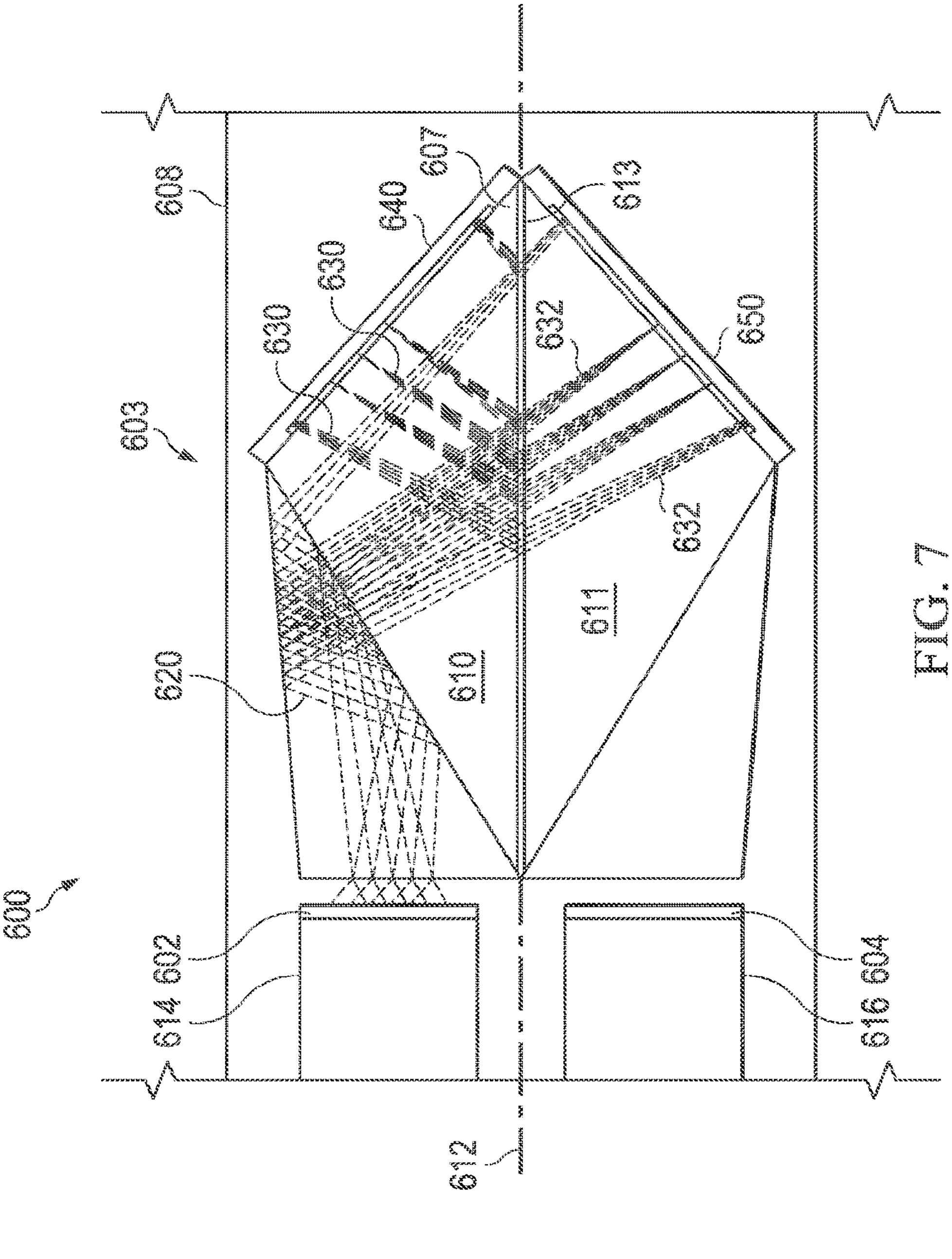
FIG. 7 is a schematic illustration of an imaging instrument include one or more shutters according to some examples.

FIG. 7 provides a schematic illustration of a stereoscopic imaging system 600 (e.g., imaging system 100) which may be a stereoscopic endoscope system that may optionally perform as a monoscopic endoscope system as described below. The stereoscopic imaging system 600 may include an imaging device 608 which may be similar to the imaging device 208 except as described. A longitudinal axis 612 may extend through the imaging device 608. The imaging device 608 may include a right objective lens assembly 614, a left objective lens assembly 616, a prism assembly 603, a right image capture sensor 640 and a left image capture sensor 650. In this example, the right objective lens assembly 614 may include a right optical control device 602, and the left objective lens assembly 616 may include a left optical control device 604. One or both of the optical control devices 602, 604 may be a dynamically controllable shutter that blocks passage of light to the prism assembly 603. A shutter may be turned on or off repeatedly throughout a medical procedure using the imaging system. In this example, the prism assembly 603 may include a two-part central prism 607 including a portion 610 and a portion 611. A coating 613 may extend between the portions 610, 611 to coat one or both of the adjacent surfaces of the portion 610, 611. The coating 613 may filter light 620, allowing reflection of selected wavelengths 630 of the light 620 and through transmission of other selected wavelengths 632 of the light 620. The coating 613 may be, for example, a dichroic coating that passes a first spectrum of wavelengths and reflects a second spectrum of wavelengths. The wavelengths 630 may be received by the right image capture sensor 640, and the wavelengths 632 may be received by the left image capture sensor 650. The optical control devices 602, 604 may include a mechanical shutter movable with an electromagnetic or piezoelectric actuator, for example. In other examples, the optical control devices 602, 604 may include liquid crystal shutters, including ferroelectric liquid crystal shutters. The shutters may be adjustable, and transparency may be controlled by a control system such as imaging control system 104. In some examples, a shutter may be present at only one of the objective lens assemblies. In the example of FIG. 7, the shutter may be positioned at a proximal end of the objective lens assembly, but in other examples, the shutter may be placed between or within optical trains of the objective lens assembly.

In one example, the imaging system 600 may use light 620 that includes wavelengths in the visible spectrum 632 and near infrared spectrums 630 to image tissue that contains a fluorescent dye. With the shutter 604 closed, the stereoscopic instrument may be rendered monoscopic, but both image capture sensors 640, 650 may be employed to process the light 620 from the single objective lens assembly 614. In this example, a dichroic filter 613 may reflect light with wavelengths greater than approximately 700 nm and may allow through passage of wavelengths less than approximately 700 nm. Thus, the near infrared light 630 may be reflected to the right image capture sensor 640 and the visible light, which may be full visible spectrum light, may be directed to the left image capture sensor 650. In this way, the right image capture sensor 640 may receive the near infrared light from the right objective lens assembly 614 and the left image capture sensor 650 may receive the full color (e.g., red/blue/green) light from the right objective lens assembly 614. Thus, the right image capture sensor 640 may be used to generate a monoscopic fluorescent image, and the left image capture sensor 650 may be used to generate a monoscopic full color image.

In another example that may combine aspects of imaging systems 500 and 600, a filter (e.g., a filter 602) may be included in the right objective lens assembly 614. The filter may, for example, have an optical density of approximately 4 or 5 at approximately 785 nm. The coating 613 may transmit wavelengths of light of approximately 400 to 796 nm with approximately 99.9% transmission of wavelengths between approximately 775 and 795. The coating 613 may reflect wavelengths of light of approximately 796 to 900 nm at a high efficiency. With the technique of this example, the sensor 650 may receive light that may be separated by a control system (e.g. the control system 104) into different images based on the detected color of light. For example, if the tissue is illuminated with visible blue light and near infrared light, the sensor 650 may detect the color white (because the color Bayer pattern on the sensor 650 is transparent at these wavelengths) corresponding to the near infrared light and the color blue corresponding to the visible blue light. The sensor 640 may detect the color white corresponding to the near infrared light. Thus, the two sensors 640, 650 may together generate a product of three sets of image data-tissue image data from the visible blue light (which may be displayed in grayscale) received at sensor 650, excitation image data from the portion of the near infrared light received at sensor 640 which may be used in an absolute determination as a metric for the amount of excitation light incident on the tissue, and an emission image data from the emission light received at sensor 650. An absolute image near infrared image may be determined from the excitation image data, the emission image data, and tissue brightness levels from the tissue image data. The emission image data may be normalized based on the local level of excitation light incident on the tissue. The result is normalized emission level image data. The normalized emission level image data may be combined with the tissue image data for presentation on a display. The presented image May encode, in the normalized emission level image data, the fluorescence of the image such that it may not exhibit fading as the fluorescent anatomy is moved to the edge of the field of view or as the instrument is moved toward or away from the tissue. This may improve communication of the fluorescence in the tissue to the viewer as it may behave in a way that is more consistent with the viewer's mental model of the scene. The blue light illumination may be turned off so that the separation of the excitation and the emission image data may be more exact since blue light may mix with the excitation light. With the blue light off, any error associated with the blue light may be removed to that the calculation of the excitation image data may be more exact and thus the calculation of the normalized emission level image data may be more precise. With the blue light turned off, the background tissue image may be unavailable.

In another example that may combine aspects of imaging systems 500 and 600, image data that corresponds to wavelengths at 660 nm, 800 nm, and 940 nm may be needed. The control system may be unable to separate the 800 and 940 nm wavelengths received at a common sensor because the sensor may perceive both wavelengths as the color white. Thus, the 660 nm wavelengths and the 940 nm wavelengths may be sent to one sensor and the 800 nm wavelengths may be sent to the other sensor. In various examples, each image capture sensor may receive three wavelength ranges corresponding to three distinct colors and the filters, coatings, and reflective surfaces of the imaging systems may be used to separate and direct the wavelength ranges toward selected image capture sensors for generating imaging data associated with the received wavelength ranges.

Figure 8:
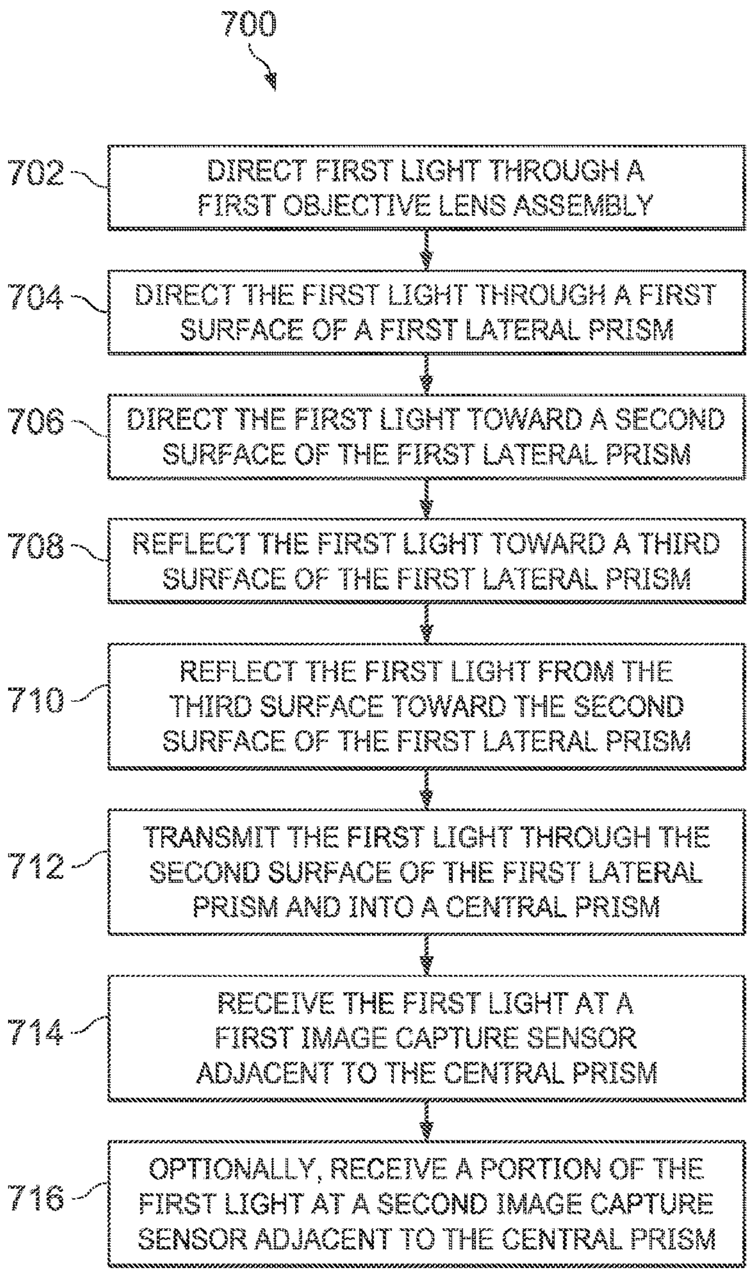
FIG. 8 is a flowchart illustrating a method of generating endoscopic images, according to some examples.

FIG. 8 is a flowchart illustrating an example method 700 for operating an imaging system, including any of those previously described. The method 700 is illustrated as a set of operations or processes. The processes illustrated in FIG. 8 may be performed in a different order than the order shown in FIG. 8, and one or more of the illustrated processes might not be performed in some embodiments of method 700. Additionally, one or more processes that are not expressly illustrated in FIG. 8 may be included before, after, in between, or as part of the illustrated processes. In some embodiments, one or more of the processes of method 700 may be implemented, at least in part, in the form of executable code stored on non-transitory, tangible, machine-readable media that when run by one or more processors (e.g., the processors of a control system) may cause the one or more processors to perform one or more of the processes.

At a process 702, first light (e.g., light 120, 220, 420, 620) may be directed through a first objective lens assembly (e.g., objective lens assembly 114, 214, 414, 514, 614) of an imaging device (e.g., imaging device 108, 208, 408, 608) such as an endoscope. Optionally, second light (e.g., light 130, 230, 430) may be directed through a second objective lens assembly (e.g., objective lens assembly 116, 216, 416, 516) of the imaging device. The objective lens assemblies may extend along opposite sides of a longitudinal axis through the imaging device.

At a process 704, the first light may be directed through a first surface (e.g., surface 204*a*) of a first lateral prism (e.g., prism 204). Optionally, the second light may be directed through a first surface (e.g., surface 206*a*) of a second lateral prism (e.g., prism 206). The first and second lateral prisms may be on opposite sides of the longitudinal axis.

At a process 706, the first light may be directed toward a second surface (e.g., surface 204*b*) of the first lateral prism. Optionally, the second light may be directed toward a second surface (e.g., surface 206*b*) of the second lateral prism.

At a process 708, the first light may be reflected or folded toward a third surface (e.g., surface 204*c*) of the first lateral prism. Optionally, the second light may be reflected toward a third surface (e.g., surface 206*c*) of the second lateral prism. Optionally, the reflections may be caused by total internal reflection at the second surface caused by an incident angle greater than a critical angle and by a lower index of refraction of a medium, such as air or a central prism, adjacent to the second surface.

At a process 710, the first light may be reflected or folded from the third surface toward the second surface of the first lateral prism. Optionally, the second light may be reflected from the third surface toward the second surface of the second lateral prism.

At a process 712, the first light may be transmitted through the second surface of the first lateral prism and into a central prism (e.g., central prism 207). Optionally, the second light may be transmitted through the second surface of the second lateral prism and into the central prism. Within the central prism, the first and second light may cross to the opposite side of the longitudinal axis.

At a process 714, the first light may be received at a first image capture sensor (e.g., image capture sensor 250, 450, 550, 650). The first image capture sensor may be on an opposite side of the longitudinal axis from the first objective lens assembly. Optionally, the second light may be received at a second image capture sensor (e.g., image capture sensor 240, 440, 540, 640). The second image capture sensor may be on an opposite side of the longitudinal axis from the second objective lens assembly.

At an optional process 716, a portion (e.g. wavelengths 630) of the first light may be received at the second image capture sensor. As described above at FIG. 7, a reflective surface within the central prism may reflect selected wavelengths of the first light to the image capture sensor 640 and pass other wavelengths of the first light to the image capture sensor 650.

Optionally, the light received at the first and/or second image capture sensors may generate image data that may be analyzed, including separated by color of light, and used to generate images for display. The image data may be displayed on a display system. The image data may be used by a computer algorithm.

In the description, specific details have been set forth describing some embodiments. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions. Not all the illustrated processes may be performed in all embodiments of the disclosed methods. Additionally, one or more processes that are not expressly illustrated in may be included before, after, in between, or as part of the illustrated processes. In some embodiments, one or more of the processes may be performed by a control system or may be implemented, at least in part, in the form of executable code stored on non-transitory, tangible, machine-readable media that when run by one or more processors may cause the one or more processors to perform one or more of the processes.

Any alterations and further modifications to the described devices, instruments, methods, and any further application of the principles of the present disclosure are fully contemplated as would normally occur to one skilled in the art to which the disclosure relates. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The systems and methods described herein may be suited for imaging, via natural or surgically created connected passageways, in any of a variety of anatomic systems, including the lung, colon, the intestines, the stomach, the liver, the kidneys and kidney calices, the brain, the heart, the circulatory system including vasculature, and/or the like. While some embodiments are provided herein with respect to medical procedures, any reference to medical or surgical instruments and medical or surgical methods is non-limiting. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

One or more elements in embodiments of this disclosure may be implemented in software to execute on a processor of a computer system such as control processing system. When implemented in software, the elements of the embodiments of this disclosure may be code segments to perform various tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and/or magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

Note that the processes and displays presented might not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

This disclosure describes various instruments, portions of instruments, and anatomic structures in terms of their state in three-dimensional space. As used herein, the term position refers to the location of an object or a portion of an object in a three-dimensional space (e.g., three degrees of translational freedom along Cartesian x-, y-, and z-coordinates). As used herein, the term orientation refers to the rotational placement of an object or a portion of an object (e.g., in one or more degrees of rotational freedom such as roll, pitch, and/or yaw). As used herein, the term pose refers to the position of an object or a portion of an object in at least one degree of translational freedom and to the orientation of that object or portion of the object in at least one degree of rotational freedom (e.g., up to six total degrees of freedom). As used herein, the term shape refers to a set of poses, positions, or orientations measured along an object.

While certain illustrative embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An endoscopic system comprising:

a first objective lens assembly extending along a first side of a central longitudinal axis through the endoscopic system;

a second objective lens assembly extending along a second side of the central longitudinal axis;

a prism assembly at a proximal end of the first and second objective lens assemblies;

a first image capture sensor coupled to the prism assembly on the first side of the central longitudinal axis; and a second image capture sensor coupled to the prism assembly on the second side of the central longitudinal axis, wherein the prism assembly directs first light from the first objective lens assembly to the second image capture sensor.

2. The endoscopic system of claim 1, wherein the prism assembly directs second light from the second objective lens assembly to the first image capture sensor.

3. The endoscopic system of claim 1, wherein an acute angle is formed between an image capture surface of the first image capture sensor and the central longitudinal axis.

4. The endoscopic system of claim 1, wherein the prism assembly includes a first lateral prism on the first side of the central longitudinal axis, a second lateral prism on the second side of the central longitudinal axis, and a central prism through which the central longitudinal axis extends.

5. The endoscopic system of claim 4, wherein the first lateral prism directs the first light toward the central prism.

6. The endoscopic system of claim 4, wherein the first lateral prism has a first refractive index and the central prism has a second refractive index and wherein the first refractive index is greater than the second refractive index.

7. The endoscopic system of claim 4, wherein the first lateral prism includes a first face, a second face, and a third face.

8. The endoscopic system of claim 7, wherein the first light enters the first lateral prism at the first face.

9. The endoscopic system of claim 8, wherein the first light is reflected, by total internal reflection at the second face, onto the third face the first lateral prism.

10. The endoscopic system of claim 9, wherein the first light is reflected by the third face toward the second face and passes through the second face.

11. The endoscopic system of claim 10, wherein the first light intersects the second face at an approximately 90 degree angle.

12. The endoscopic system of claim 1, wherein the first objective lens assembly includes a first entrance pupil and the second objective lens assembly includes a second entrance pupil and wherein a distance between centers of the first and second entrance pupils are between approximately 1 and 6 mm.

13. The endoscopic system of claim 1, further comprising a first heat dissipation component coupled to the first image capture sensor and extending along the first side of the central longitudinal axis and a second heat dissipation component coupled to the second image capture sensor and extending along the second side of the central longitudinal axis.

14. The endoscopic system of claim 1, further comprising an endoscopic housing and a scaffold to which the first objective lens assembly, the second objective lens assembly and the prism assembly are coupled, wherein the scaffold extends between the endoscopic housing and the first objective lens assembly, the second objective lens assembly and the prism assembly.

15. The endoscopic system of claim 1, wherein the prism assembly includes a central prism that directs a first portion of the first light to the second image capture sensor and directs a second portion of the first light to the first image capture sensor.

16. The endoscopic system of claim 15, wherein the central prism includes a first prism portion on the first side of the central longitudinal axis and a second prism portion on the second side of the central longitudinal axis.

17. The endoscopic system of claim 16, wherein the first prism portion includes a first central face covered with a dichroic coating.

18. The endoscopic system of claim 16, further comprising a shutter that blocks second light traveling through the second objective lens assembly prior to reaching the prism assembly.

19. The endoscopic system of claim 18, wherein the shutter includes a liquid crystal shutter, a ferroelectric shutter, or a piezoelectric shutter.

20. The endoscopic system of claim 15, wherein the first portion of the first light is infrared light.

* * * * *